(12) United States Patent
Lee

(10) Patent No.: US 12,350,068 B2
(45) Date of Patent: Jul. 8, 2025

(54) MAGNETIC RESONANCE IMAGING DEVICE AND METHOD FOR PRECISELY MEASURING CEREBRAL OXYGEN METABOLISM

(71) Applicant: KYUNGPOOK NATIONAL UNIVERSITY INDUSTRY—ACADEMIC COOPERATION FOUNDATION, Daegu (KR)

(72) Inventor: Hyunyeol Lee, Daegu (KR)

(73) Assignee: KYUNGPOOK NATIONAL UNIVERSITY INDUSTRY—ACADEMIC COOPERATION, Daegu (KR)

( * ) Notice: Subject to any disclaimer, the term of this patent is extended or adjusted under 35 U.S.C. 154(b) by 0 days.

(21) Appl. No.: 18/288,730

(22) PCT Filed: Apr. 11, 2022

(86) PCT No.: PCT/KR2022/005168
§ 371 (c)(1),
(2) Date: Oct. 27, 2023

(87) PCT Pub. No.: WO2022/231167
PCT Pub. Date: Nov. 3, 2022

(65) Prior Publication Data
US 2024/0206808 A1 Jun. 27, 2024

(30) Foreign Application Priority Data
Apr. 29, 2021 (KR) .................. 10-2021-0055882

(51) Int. Cl.
*A61B 5/00* (2006.01)
*A61B 5/055* (2006.01)
*G01R 33/56* (2006.01)

(52) U.S. Cl.
CPC .......... *A61B 5/4866* (2013.01); *A61B 5/0042* (2013.01); *A61B 5/055* (2013.01); *G01R 33/56* (2013.01)

(58) Field of Classification Search
CPC ..... A61B 5/4866; A61B 5/0042; A61B 5/055; G01R 33/56366; G01R 33/4816; G01R 33/5613; G01R 33/4826; G01R 33/50
See application file for complete search history.

(56) References Cited

U.S. PATENT DOCUMENTS

2010/0030062 A1  2/2010  Bolar et al.

FOREIGN PATENT DOCUMENTS

KR  10-1008041 B1  1/2011
KR  10-2017-0003061 A  1/2017
(Continued)

OTHER PUBLICATIONS

"Quantitative Mapping of Cerebral Metabolic Rate of Oxygen (CMRO2) using Quantitative Susceptibility Mapping (QSM)" by J. Zhang et al. Magn Reson Med. 74(4). p. 945-952. (Year: 2015).*
(Continued)

*Primary Examiner* — Jason M Ip
(74) *Attorney, Agent, or Firm* — Sughrue Mion, PLLC

(57) ABSTRACT

A magnetic resonance imaging device for measuring cerebral oxygen metabolism includes a memory configured to store computer-readable instructions and one or more processors configured to execute the instructions such that the one or more processors is configured to acquire UTE (ultrashort echo-time)-AUSFIDE (alternating unbalanced SSFP-FID & SSFP-ECHO) image data, VS-VSL (velocity-selective venous spin labeling) image data, and pCASL (pseudo-continuous arterial spin labeling) image data, process a plurality of preliminary information data for quantitative model processing and process CBF (cerebral blood flow)

(Continued)

information data, acquire variable information (Yv) to derive an oxygen extraction fraction (OEF) and a cerebral metabolic rate of oxygen ($CMRO_2$) in order to acquire a 3-dimensional oxygen metabolic rate map of an entire brain, derive the oxygen extraction fraction (OEF) and the cerebral metabolic rate of oxygen ($CMRO_2$) and generate an oxygen metabolic rate map image as a magnetic resonance image.

13 Claims, 5 Drawing Sheets

(56) References Cited

FOREIGN PATENT DOCUMENTS

| KR | 10-2174092 B1 | 11/2020 |
|----|---------------|---------|
| KR | 10-2211050 B1 | 2/2021  |

OTHER PUBLICATIONS

"Arterial spin labeling for the measurement of cerebral perfusion and angiography" by P. Jezzard et al, JCBFM, vol. 38(4). p. 603-626. (Year: 2018).*

"3D CMRO2 mapping in human brain with direct 17O MRI: Comparison of conventional and proton-constrained reconstructions" by D. Kurzhunov et al. NeuroImage. 155, p. 612-624. (Year: 2017).*

"Measurement of OEF and absolute CMRO2: MRI-based methods using interleaved and combined hypercapnia and hyperoxia" by R.G. Wise et al. NeuroImage. 83. p. 135-147. (Year: 2013).*

Sung-Jin Kang, et al., "Overview of Arterial Spin Labeling Perfusion MRI", Journal of the Korean Magnetics Society, 2017, pp. 145-152, vol. 27, No. 4.

International Search Report for PCT/KR2022/005168 dated Jul. 7, 2022 [PCT/ISA/210].

* cited by examiner

MAGNETIC RESONANCE IMAGING DEVICE AND METHOD FOR PRECISELY MEASURING CEREBRAL OXYGEN METABOLISM

This application is a National Stage Entry of PCT International Application No. PCT/KR2022/005168, which was filed on Apr. 11, 2022, and which claims priority to Korean Patent Application No. 10-2021-0055882, filed on Apr. 29, 2021 in the Korean Intellectual Property Office, the disclosure of which is incorporated herein by reference.

TECHNICAL FIELD

The present disclosure relates to a three-dimensional quantitative magnetic resonance imaging scheme for precisely measuring cerebral oxygen metabolism and, more particularly, to a quantitative magnetic resonance imaging scheme which can precisely measure cerebral oxygen metabolism in three dimensions throughout an entire brain region using multi-echo ultrashort echo-time (UTE)-alternating unbalanced SSFP-FID & SSFP-ECHO (AUSFIDE) image data, a plurality of measurement data to be pre-processed, and separately acquired cerebral blood volume information data.

BACKGROUND ART

The cerebral oxygen metabolic activity may usually be expressed based on a $CMRO_2$ (cerebral metabolic rate of oxygen) parameter. It is well known that the cerebral oxygen metabolic activity may change under sleep and over aging in healthy brains as well as in neurological disease states.

Therefore, precisely measuring the $CMRO_2$ (cerebral metabolic rate of oxygen) may lead to broad understanding of brain physiology in healthy brains as well as in neurological disease states.

However, because brain metabolism is closely related to arterial blood oxygen supply and capillary oxygen extraction, it is difficult to directly measure $CMRO_2$ (cerebral metabolic rate of oxygen). Rather, the $CMRO_2$ (cerebral metabolic rate of oxygen) may be calculated indirectly based on the Fick's principle of a following Mathematical Relationship 1.

$$CMRO_2 = C_a \cdot CBF \cdot (Y_a - Y_v) \qquad \text{[Mathematical Relationship 1]}$$

In the Mathematical Relationship 1, Ca may represent an oxygen capacity of arterial blood, CBF (cerebral blood flow) may represent cerebral blood flow, and Ya may represent an arterial blood hemoglobin oxygen saturation level, and Yv may represent a venous blood hemoglobin oxygen saturation level.

To calculate the $CMRO_2$ from Mathematical Relationship 1, CBF and oxygen extraction fraction (OEF) information should be acquired. The oxygen extraction fraction may be calculated as a ratio of (the arterial blood hemoglobin oxygen saturation level-the venous blood hemoglobin oxygen saturation level) to the arterial blood hemoglobin oxygen saturation level.

A scheme using positron emission tomography (PET) imaging equipment is often considered as a standard scheme for measuring the $CMRO_2$ based on an area.

In this scheme, a radio tracer of oxygen ($O_2$) and hydrogen dioxide ($H_2O_2$) is inserted into the human body to acquire the OEF information and the CBF information, this scheme is not considered a completely non-invasive method.

Furthermore, as it is difficult to use the PET-based $CMRO_2$ measurement method in actual clinical settings due to radiation exposure, a very long imaging time, high cost for experimental preparation, and complexity thereof, MIR-based schemes as a practical and non-invasive alternative to PET are starting to emerge.

qBOLD (quantitative blood oxygen level dependent) MRI (Magnetic Resonance Image) is a representative technology for measuring OEF, and is based on a MRI signal change model under the surrounding magnetic field disturbance effect of deoxygenated hemoglobin (dHb).

In this regard, a time constant representing the signal change is denoted as R2', and corresponds to an RF-inversion possible portion of a transverse relaxation rate constant R2*(R2'=R2*−R2). R2' may have a linear relationship with the CBVv and the venous blood dHb concentration ($[dHb]v \propto (1-Yv)$) as shown in a following Mathematical Relationship 2.

$$R'_2 \propto CBV_v \cdot [dHb]_v \qquad \text{[Mathematical Relationship 2]}$$

The qBOLD method acquires multiple echoes from a magnetic resonance pulse train sensitive to R2', calculates R2' of each pixel via signal analysis, and uses a spin echo surrounding signal to divide the measured R2' into CBVv and Yv.

Therefore, qBOLD may be considered the only technology that maps the brain's OEF in a completely non-invasive scheme without patient intervention.

However, due to the mutual coupling effect between the two factors CBVv and [dHb] v that constitute the Mathematical Relationship 2, it is very difficult to obtain a unique solution using the conventional qBOLD scheme. Thus, unless a signal-to-noise ratio of the image signal is very high, the reproducibility of the derived OEF information is limited.

In addition, because the existing qBOLD method does not consider the effect of a non-heme iron component on R2' of a tissue at all, a large measurement error may occur in a deep brain area where the non-heme iron is heavily deposited, such as the basal ganglia.

Furthermore, in an air dense tissue with high magnetic field non-uniformity, the acquired signal is severely deformed, making it very difficult to correctly analyze a time series signal.

DISCLOSURE

Technical Purpose

A purpose of the present disclosure is to precisely measure a high-resolution 3-dimensional oxygen metabolic rate throughout the entire brain by generating a quantitative magnetic resonance image that enables precise measurement of cerebral oxygen metabolism in a 3-dimensional manner throughout the entire brain using multi-echo UTE (ultrashort echo-time)-AUSFIDE (alternating unbalanced SSFP-FID & SSFP-ECHO) image data, a plurality of measurement data to be pre-processed, and separately acquired cerebral blood volume information data.

Furthermore, a purpose of the present disclosure is to generate a magnetic resonance image capable of 3-dimensional mapping of the entire brain based on the parameters of the cerebral blood volume, the oxygen extraction fraction, and the cerebral metabolic rate of oxygen (CMRO$_2$), under the endogenous contrast mechanism.

Further, a purpose of the present disclosure is to generate a magnetic resonance image capable of distinguishing a contribution of an RF-reversible transverse relaxation rate constant of a non-heme iron and a contribution of the RF-reversible transverse relaxation rate constant of a heme iron from each other, and accurately distinguishing a cerebral blood volume and a venous blood oxygen saturation level from each other.

Further, a purpose of present disclosure is to improve an image resolution in a longitudinal direction to derive an isotropic high-resolution parameter map, and generate an image with a reduced level of signal distortion due to non-spontaneous movement in the imaging target such as blood flow or cerebrospinal fluid flow, and acquire the UTE (ultrashort echo-time) signal, and thus improve the qBOLD (quantitative blood oxygen level dependent) model signal analysis performance without increasing a total imaging time using the acquired UTE signal instead of the spin echo information required in the process of processing the qBOLD (quantitative blood oxygen level dependent) model as the quantitative model.

Technical Solution

A magnetic resonance imaging device according to one embodiment of the preset disclosure may include a data acquisition unit configured to acquire UTE (ultrashort echo-time)-AUSFIDE (alternating unbalanced SSFP-FID & SSFP-ECHO) image data, VS-VSL (velocity-selective venous spin labeling) image data, and pCASL (pseudo-continuous arterial spin labeling) image data: data pre-processing unit configured to process a plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data, and to process CBF (cerebral blood flow) information data based on the acquired pCASL (pseudo-continuous arterial spin labeling) image data: quantitative model processing unit configured to acquire variable information (Yv) to derive an oxygen extraction fraction (OEF) and a cerebral metabolic rate of oxygen (CMRO$_2$) in order to acquire a 3-dimensional oxygen metabolic rate map of an entire brain using the processed plurality of preliminary information data; and an image generation unit configured to derive the oxygen extraction fraction (OEF) and the cerebral metabolic rate of oxygen (CMRO$_2$) using the acquired variable information and to generate an oxygen metabolic rate map image as a magnetic resonance image, based on the derived oxygen extraction fraction (OEF) and the derived cerebral metabolic rate of oxygen (CMRO$_2$).

The data acquisition unit may be configured to acquire the UTE (ultrashort echo-time)-AUSFIDE (alternating unbalanced SSFP-FID & SSFP-ECHO) image data to estimate at least one of an RF-reversible transverse relaxation rate constant, an RF-irreversible transverse relaxation rate constant, a susceptibility, and an induced magnetic field offset.

The data pre-processing unit may be configured to: process the induced magnetic field offset based on a voxel spread function (VSF) as first preliminary information data among the plurality of preliminary information data, using the acquired UTE (ultrashort echo-time)-AUSFIDE (alternating unbalanced SSFP-FID & SSFP-ECHO) image data; alternately collect a SSFP-FID signal and a SSFP-ECHO signal and process the RF-reversible transverse relaxation rate constant and the RF-irreversible transverse relaxation rate constant as second preliminary information data thereof, using the alternately collected SSFP-FID signal and a SSFP-ECHO signal; and process the susceptibility as third preliminary information data thereof, based on quantitative susceptibility mapping (QSM).

The data pre-processing unit may be configured to process cerebral blood volume (CBVv) information data among the plurality of preliminary information data, based on the VS-VSL (velocity-selective venous spin labeling) image data.

The quantitative model processing unit may be configured to apply the plurality of preliminary information data to a following Mathematical Relationship 3 to acquire the variable information (Yv) so as to include a contribution distinguishing term distinguishing a contribution of an RF-reversible transverse relaxation rate constant of a non-heme iron and a contribution of the RF-reversible transverse relaxation rate constant of a heme iron from each other:

$$\mathrm{argmin} \sum_t \|y(t) - \Xi(\Theta, t)\|_2^2 + w\|\chi - \Psi(\Theta)\|_2^2 + p\|R_2' - \Upsilon(\Theta)\|_2^2 \quad \text{[Mathematical Relationship 3]}$$

The quantitative model processing unit may be configured to acquire the contribution distinguishing term using a following Mathematical Relationship 5 in acquiring the variable information (Yv) based on the Mathematical Relationship 3:

$$\Upsilon = R'_{2,nh} + R'_{2,h}; R'_{2,h} \propto CBV_v \cdot (1 - Y_v). \quad \text{[Mathematical Relationship 5]}$$

The image generation unit may be configured to derive the oxygen extraction fraction (OEF) using an arterial blood oxygen saturation level (Ya) based on pulse oximetry, and the variable information (Yv).

The image generation unit may be configured to derive the cerebral metabolic rate of oxygen (CMRO$_2$) using the processed CBF (cerebral blood flow) information data, the derived oxygen extraction fraction (OEF), an oxygen capacity (Ca) of arterial blood, and the variable information (Yv).

A magnetic resonance imaging method for precisely measuring cerebral oxygen metabolism according to one embodiment of the preset disclosure may include acquiring, by a data acquisition unit, UTE (ultrashort echo-time)-AUSFIDE (alternating unbalanced SSFP-FID & SSFP-ECHO) image data, VS-VSL (velocity-selective venous spin labeling) image data, and pCASL (pseudo-continuous arterial spin labeling) image data; processing, by a data pre-processing unit, a plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data, and processing, by the data pre-processing unit, CBF (cerebral blood flow) information data based on the acquired pCASL (pseudo-continuous arterial spin labeling) image data; acquiring, by a quantitative model processing unit, variable information (Yv) to derive an oxygen extraction fraction (OEF) and a cerebral metabolic rate of oxygen (CMRO$_2$) in order to acquire a 3-dimensional oxygen metabolic rate map of an entire brain using the processed plurality of preliminary information data; and deriving, by an image generation unit, the oxygen extraction fraction (OEF) and the cerebral metabolic rate of oxygen (CMRO$_2$) using the acquired variable information and generating, by the image generation unit, an oxygen metabolic rate map image as a magnetic resonance image, based on the derived oxygen extraction fraction (OEF) and the derived cerebral metabolic rate of oxygen (CMRO$_2$).

Acquiring, by the data acquisition unit, the UTE (ultra-short echo-time)-AUSFIDE (alternating unbalanced SSFP-FID & SSFP-ECHO) image data, the VS-VSL (velocity-selective venous spin labeling) image data, and the pCASL (pseudo-continuous arterial spin labeling) image data may include: acquiring, by the data acquisition unit, the UTE (ultrashort echo-time)-AUSFIDE (alternating unbalanced SSFP-FID & SSFP-ECHO) image data to estimate at least one of an RF-reversible transverse relaxation rate constant, an RF-irreversible transverse relaxation rate constant, a susceptibility, and an induced magnetic field offset.

Processing, by the data pre-processing unit, the plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data may include: processing, by the data pre-processing unit, the induced magnetic field offset based on a voxel spread function (VSF) as first preliminary information data among the plurality of preliminary information data, using the acquired UTE (ultrashort echo-time)-AUSFIDE (alternating unbalanced SSFP-FID & SSFP-ECHO) image data: alternately collecting, by the data pre-processing unit, a SSFP-FID signal and a SSFP-ECHO signal and processing, by the data pre-processing unit, the RF-reversible transverse relaxation rate constant and the RF-irreversible transverse relaxation rate constant as second preliminary information data thereof, using the alternately collected SSFP-FID signal and a SSFP-ECHO signal; and processing, by the data pre-processing unit, the susceptibility as third preliminary information data thereof, based on quantitative susceptibility mapping (QSM).

Acquiring, by the quantitative model processing unit, the variable information (Yv) to derive the oxygen extraction fraction (OEF) and the cerebral metabolic rate of oxygen (CMRO$_2$) in order to acquire the 3-dimensional oxygen metabolic rate map of an entire brain using the processed plurality of preliminary information data may include: applying, by the quantitative model processing unit, the plurality of preliminary information data to a following Mathematical Relationship 3 to acquire the variable information (Yv) so as to include a contribution distinguishing term distinguishing a contribution of an RF-reversible transverse relaxation rate constant of a non-heme iron and a contribution of the RF-reversible transverse relaxation rate constant of a heme iron from each other:

$$\operatorname{argmin} \sum_t \|y(t) - \Xi(\Theta, t)\|_2^2 + w\|\chi - \Psi(\Theta)\|_2^2 + p\|R_2' - \Upsilon(\Theta)\|_2^2 \quad \text{[Mathematical Relationship 3]}$$

Acquiring, by the quantitative model processing unit, the variable information (Yv) to derive the oxygen extraction fraction (OEF) and the cerebral metabolic rate of oxygen (CMRO$_2$) in order to acquire the 3-dimensional oxygen metabolic rate map of an entire brain using the processed plurality of preliminary information data may include: acquiring, by the quantitative model processing unit, the contribution distinguishing term using a following Mathematical Relationship 5 in acquiring the variable information (Yv) based on the Mathematical Relationship 3:

$$Y = R'_{2,nh} + R'_{2,h}; R'_{2,h} \propto CBV_v \cdot (1 - Y_v). \quad \text{[Mathematical Relationship 5]}$$

Deriving, by the image generation unit, the oxygen extraction fraction (OEF) and the cerebral metabolic rate of oxygen (CMRO$_2$) using the acquired variable information and generating, by the image generation unit, the oxygen metabolic rate map image as the magnetic resonance image, based on the derived oxygen extraction fraction (OEF) and the derived cerebral metabolic rate of oxygen (CMRO$_2$) may include: deriving, by the image generation unit, the oxygen extraction fraction (OEF) using an arterial blood oxygen saturation level (Ya) based on pulse oximetry, and the variable information (Yv); and deriving, by the image generation unit, the cerebral metabolic rate of oxygen (CMRO$_2$) using the processed CBF (cerebral blood flow) information data, the derived oxygen extraction fraction (OEF), an oxygen capacity (Ca) of arterial blood, and the variable information (Yv).

Technical Effect

The device and the method of the present disclosure may precisely measure a high-resolution 3-dimensional oxygen metabolic rate throughout the entire brain by generating a quantitative magnetic resonance image that enables precise measurement of cerebral oxygen metabolism in a 3-dimensional manner throughout the entire brain using multi-echo UTE (ultrashort echo-time)-AUSFIDE (alternating unbalanced SSFP-FID & SSFP-ECHO) image data, a plurality of measurement data to be pre-processed, and separately acquired cerebral blood volume information data.

Furthermore, the device and the method of the present disclosure may generate a magnetic resonance image capable of 3-dimensional mapping of the entire brain based on the parameters of the cerebral blood volume, the oxygen extraction fraction, and the cerebral metabolic rate of oxygen (CMRO$_2$), under the endogenous contrast mechanism.

Further, the device and the method of the present disclosure may generate a magnetic resonance image capable of distinguishing a contribution of an RF-reversible transverse relaxation rate constant of a non-heme iron and a contribution of the RF-reversible transverse relaxation rate constant of a heme iron from each other, and accurately distinguishing a cerebral blood volume and a venous blood oxygen saturation level from each other.

Further, the device and the method of present disclosure may improve an image resolution in a longitudinal direction to derive an isotropic high-resolution parameter map, and generate an image with a reduced level of signal distortion due to non-spontaneous movement in the imaging target such as blood flow or cerebrospinal fluid flow, and acquire the UTE (ultrashort echo-time) signal, and thus improve the qBOLD (quantitative blood oxygen level dependent) model signal analysis performance without increasing a total imaging time using the acquired UTE signal instead of the spin echo information required in the process of processing the qBOLD (quantitative blood oxygen level dependent) model as the quantitative model.

BEST MODE

Figure 1:
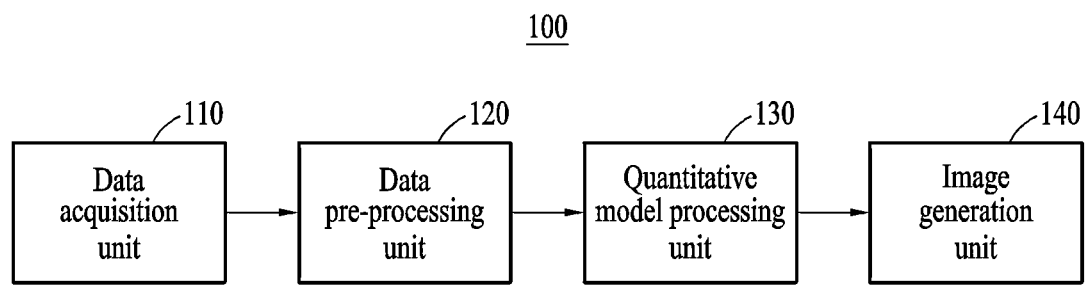
FIG. 1 illustrates a magnetic resonance imaging device for precisely measuring cerebral oxygen metabolism according to an embodiment of the present disclosure.

Specific structural and functional descriptions of embodiments according to the concept of the present disclosure disclosed herein are merely illustrative for the purpose of explaining the embodiments according to the concept of the present disclosure. Furthermore, the embodiments according to the concept of the present disclosure can be implemented in various forms and the present disclosure is not limited to the embodiments described herein. The embodiments according to the concept of the present disclosure may be implemented in various forms as various modifications may be made. The embodiments will be described in detail herein with reference to the drawings. However, it should be understood that the present disclosure is not limited to the embodiments according to the concept of the present disclosure, but includes changes, equivalents, or alternatives falling within the spirit and scope of the present disclosure.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the scope of rights according to the concept of the present invention.

It will be understood that when an element is referred to as being "on", "connected to" or "coupled to" another element, it may be directly on, connected or coupled to the other element or intervening elements may be present. In contrast, when an element is referred to as being "directly on," "directly connected to" or "directly coupled to" another element or layer, there are no intervening elements or layers present. Other words used to describe the relationship between elements should be interpreted in a like fashion (e.g., "between," versus "directly between," "adjacent," versus "directly adjacent," etc.).

The terms used in the present specification are used to explain a specific exemplary embodiment and not to limit the present inventive concept. Thus, the expression of singularity in the present specification includes the expression of plurality unless clearly specified otherwise in context. Also, terms such as "include" or "comprise" in the specification should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure will now be described more fully with reference to the accompanying drawings, in which exemplary embodiments of the invention are shown. This disclosure may, however, be embodied in many different forms and should not be construed as limited to the exemplary embodiments set forth herein. Like reference numerals in the drawings denote like elements.

FIG. 1 illustrates a magnetic resonance imaging device for precisely measuring cerebral oxygen metabolism according to an embodiment of the present disclosure.

FIG. 1 illustrates components of a magnetic resonance imaging device for precisely measuring cerebral oxygen metabolism according to an embodiment of the present disclosure.

Referring to FIG. 1, a magnetic resonance imaging device 100 according to an embodiment of the present disclosure includes a data acquisition unit 110, a data pre-processing unit 120, a quantitative model processing unit 130, and an image generation unit 140.

According to one embodiment of the present disclosure, the data acquisition unit 110 may acquire UTE (ultrashort echo-time)-AUSFIDE (alternating unbalanced SSFP-FID & SSFP-ECHO) image data, VS-VSL (velocity-selective venous spin labeling) image data and pCASL (pseudo-continuous arterial spin labeling) image data.

In one example, the data acquisition unit 110 may acquire UTE-AUSFIDE image data to estimate at least one of an RF-irreversible transverse relaxation rate constant (R2), an RF-reversible transverse relaxation rate constant (R2'), a susceptibility ($\chi$), and an induced magnetic field offset ($\Delta B_0$).

According to one embodiment of the present disclosure, the data acquisition unit 110 may acquire the UTE-AUSFIDE image data by sampling data in a 3D full radial trajectory data in an ultrashort echo-time.

According to one embodiment of the present disclosure, the data pre-processing unit 120 processes a plurality of preliminary information data for quantitative model processing.

Specifically, the data pre-processing unit 120 may process the plurality of preliminary information data for quantitative model processing, based on the acquired UTE-AUSFIDE image data and the acquired VS-VSL image data, and may process CBF (cerebral blood flow) information data based on the acquired pCASL image data.

In one example, using the UTE-AUSFIDE image data, the data pre-processing unit 120 may process the induced magnetic field offset based on a voxel spread function (VSF) as first preliminary information data among the plurality of preliminary information data. The data pre-processing unit 120 may collect alternately the SSFP-FID signal and the SSFP-ECHO signal and may process the RF-reversible transverse relaxation rate constant and the RF-irreversible transverse relaxation rate constant as second preliminary information data thereof, using the collection result. The data pre-processing unit 120 may process the susceptibility as third preliminary information data thereof, based on quantitative susceptibility mapping (QSM).

For example, the data pre-processing unit 120 may process cerebral blood volume (CBVv) information data among the plurality of preliminary information data, based on the VS-VSL image data.

According to one embodiment of the present disclosure, the quantitative model processing unit 130 may acquire variable information (Yv) to derive the oxygen extraction fraction (OEF) and the cerebral metabolic rate of oxygen (CMRO$_2$) in order to acquire a 3-dimensional oxygen metabolic rate map of the entire brain using the plurality of preliminary information data processed by the data preprocessing unit 120.

In one example, the quantitative model processing unit 130 may apply the plurality of preliminary information data to a following Mathematical Relationship 3 to acquire the variable information (Yv) so as to include a contribution distinguishing term which distinguishes the contribution of the RF-reversible transverse relaxation rate constant of the non-heme iron and the contribution of the RF-reversible transverse relaxation rate constant of the heme iron from each other:

$$\operatorname{argmin} \sum_t \|y(t) - \Xi(\Theta, t)\|_2^2 + \quad \text{[Mathematical Relationship 3]}$$
$$w\|\chi - \Psi(\Theta)\|_2^2 + p\|R'_2 - \Upsilon(\Theta)\|_2^2$$

In the Mathematical Relationship 3, y(t) may represent the sampling time of the AUSFIDE (alternating unbalanced SSFP-FID & SSFP-ECHO) image data signal, $\Theta = \{S_{FID}, S_{ECHO}\}$ may represent a description of R2 and R2', and $\Psi$ may represent a four pool decomposition model for Y that distinguishes the contribution of the R2' of non-blood (R'$_{2,nb}$) and the contribution of the R2' of deoxygenated blood (DBV) from each other. w and p may represent normalization parameters that apply preliminary knowledge in qBOLD parameter estimation. θ={Yv,CBVv,R2,nh,xnb} may represent a set of unknowns, and γ may represent the term for distinguishing the contribution of the RF-reversible transverse relaxation rate constant R2' of the non-heme iron (nh) and the contribution of the RF-reversible transverse relaxation rate constant R2' of the heme iron (h) from each other.

For example, in the VS-VSL scheme, an error may occur when measuring CBVv. Thus, the CBVv preliminary information may be repeatedly updated in the process of finding a solution to the Mathematical Relationship 3. Thus, the error may be reduced.

Numerical simulation may be performed, and thus the effectiveness of the approach that provides the preliminary information in the qBOLD problem may be evaluated based on the numerical simulation result.

To this end, the UTE-AUSFIDE signal may be simulated using related physiological and image parameters and noise may be added thereto, and then, the solution to the Mathematical Relationship 3 may be obtained in following four ways:
- First, w=p=0, preliminary CBVv non-utilization (conventional qBOLD scheme) may be used.
- Second, w>0, p=0, preliminary CBVv non-utilization (qBOLD+QSM method) may be used.
- Third, w>0, p>0, preliminary CBVv non-utilization may be used.
- Fourth, w>, p>0, preliminary CBVv utilization may be used. The resulting values of the above four cases may be compared to the truth value using the mean square error.

In addition, an error within a certain range may be added to the preliminary values CBVv and R2' and then the Mathematical Relationship 3 may be solved based on the values obtained by adding the error thereto. Thus, the effect of the preliminary information on potential errors may be evaluated based on the thus obtained solution.

The four pool decomposition model for $\Psi$ as described above may be specified using a following Mathematical Relationship 4. γ may be specified using a following Mathematical Relationship 5:

$$\Psi = \frac{DBV}{\alpha}\beta_{Hb} \quad \text{[Mathematical Relationship 4]}$$
$$[\chi_{oHb} + \Delta\chi_{Hb}\{\alpha(1-Y_v) + (1-\alpha)(1-Y_a)\}] +$$
$$\frac{DBV}{\alpha}(1-\beta_{Hb})\chi_p + \left(1 - \frac{DBV}{\alpha}\right)\chi_{nb}$$

In the Mathematical Relationship 4, α may represent the ratio of DBV to a total cerebral blood volume, $\Delta_{x0}$ may represent a difference between a susceptibility of deoxygenated blood and a susceptibility of oxygen-containing blood, and $\Delta_{xHb}$ may represent a difference between a susceptibility of deoxygenated hemoglobin and a susceptibility of oxygen-containing blood. The $x_{ba}$, $x_{oHb}$, and $x_p$ may respectively represent susceptibilities of fully oxygenated blood, oxyhemoglobin, and plasma.

According to one embodiment of the present disclosure, the quantitative model processing unit 130 may acquire the variable information (Yv) based on the Mathematical Relationship 3 and acquire the contribution distinguishing term based on a following Mathematical Relationship 5:

$$\Upsilon = R'_{2,nh} + R'_{2,h}; R'_{2,h} \propto CBV_v \cdot (1 - Y_v). \quad \text{[Mathematical Relationship 5]}$$

In the mathematical Relationship 5, γ may distinguish the contribution of R2' of non-blood and the contribution of R2' of deoxygenated blood from each other. R2'(R'2,h) of the deoxygenated blood is correlated with CBVv and Yv.

The SSFP-FID signal may be expressed as a following Mathematical Relationship 6. The SSFP-ECHO signal may be expressed as a following Mathematical Relationship 7:

$$S_{FID}(t_{FID}) = S_0 e^{-(R_2 + R'_{2,nb})t_{FID}} \quad \text{[Mathematical Relationship 6]}$$
$$F_{qBOLD}(\Theta, t_{FID})F_{VSF}(\Delta B_0, t_{FID})$$

In the Mathematical Relationship 6, FqBOLD may be expressed as ta following Mathematical Relationship 8. t may represent a time, FVSF may represent a voxel spread function. $\Delta B_0$ may represent change in the induced magnetic field offset.

$$S_E(t_{ECHO}) = \delta S_0 e^{(R_2 - R'_{2,nb})t_{ECHO}} \quad \text{[Mathematical Relationship 7]}$$
$$F_{qBOLD}(\Theta, t_{ECHO})F_{VSF}(\Delta B_0, t_{ECHO})$$

In the Mathematical Relationship 7, FqBOLD may be expressed as the following Mathematical Relationship 8. t may represent a time, and FVSF may represent the voxel spread function, and $\Delta B_0$ may represent the change in the induced magnetic field offset.

$$F_{qBOLD}(t) = e^{-DBV \cdot f(t/t_c)};$$ [Mathematical Relationship 8]

$$t_c^{-1} = \frac{4\pi}{3}\gamma B_0 \Delta \chi_0 Hct(1 - Y_v) + \chi_{nb} - \chi_{ba}$$

In the Mathematical Relationship 8, α may represent the ratio of DBV to the total cerebral blood volume. $\Delta x_0$ may represent a difference between a susceptibility of deoxygenated blood and a susceptibility of oxygen-containing blood, and $\Delta_{xHb}$ may represent a difference between a susceptibility of deoxygenated hemoglobin and a susceptibility of oxygen-containing blood. The $x_{ba}$, $x_{oHb}$, and $x_p$ may respectively represent susceptibilities of fully oxygenated blood, oxyhemoglobin, and plasma.

According to one embodiment of the present disclosure, the image generation unit 140 may derive the oxygen extraction fraction (OEF) and the cerebral metabolic rate of oxygen ($CMRO_2$) using the variable information acquired from the quantitative model processing unit 130 and may generate an oxygen metabolic rate map image as a magnetic resonance image using the derived oxygen extraction fraction (OEF) and the derived cerebral metabolic rate of oxygen ($CMRO_2$).

In one example, the image generation unit 140 may derive the oxygen extraction fraction (OEF) using the arterial blood oxygen saturation level Ya based on pulse oximetry and the variable information (Yv).

According to one embodiment of the present disclosure, the image generation unit 140 may derive the cerebral metabolic rate of oxygen ($CMRO_2$) using the processed cerebral blood flow (CBF) information data, the derived oxygen extraction fraction (OEF), the oxygen capacity Ca of arterial blood, and the variable information (Yv).

The magnetic resonance imaging device 100 according to an embodiment of the present disclosure may acquire the data using a UTE-AUSFIDE pulse train, and acquire the CBVv estimate separately from the parameters (R2, R2', χ, $\Delta B_0$) measured from the acquired data, and thus may solve the pre-constrained qBOLD problem using the parameters and the CBVv estimate. Thus, the magnetic resonance imaging device 100 may improve the measurement accuracy of the oxygen extraction fraction (OEF) and the cerebral metabolic rate of oxygen ($CMRO_2$).

In other words, the magnetic resonance imaging device according to an embodiment of the present disclosure may precisely measure a high-resolution 3-dimensional oxygen metabolic rate throughout the entire brain by generating a quantitative magnetic resonance image that enables precise measurement of cerebral oxygen metabolism in a 3-dimensional manner throughout the entire brain using the multi-echo UTE (ultrashort echo-time)-AUSFIDE (alternating unbalanced SSFP-FID & SSFP-ECHO) image data, the plurality of measurement data to be pre-processed, and the separately acquired cerebral blood volume information data.

Furthermore, the magnetic resonance imaging device according to an embodiment of the present disclosure may generate a magnetic resonance image capable of 3-dimensional mapping of the entire brain based on the parameters of the cerebral blood volume, the oxygen extraction fraction, and the cerebral metabolic rate of oxygen ($CMRO_2$), under the endogenous contrast mechanism.

Figure 2:
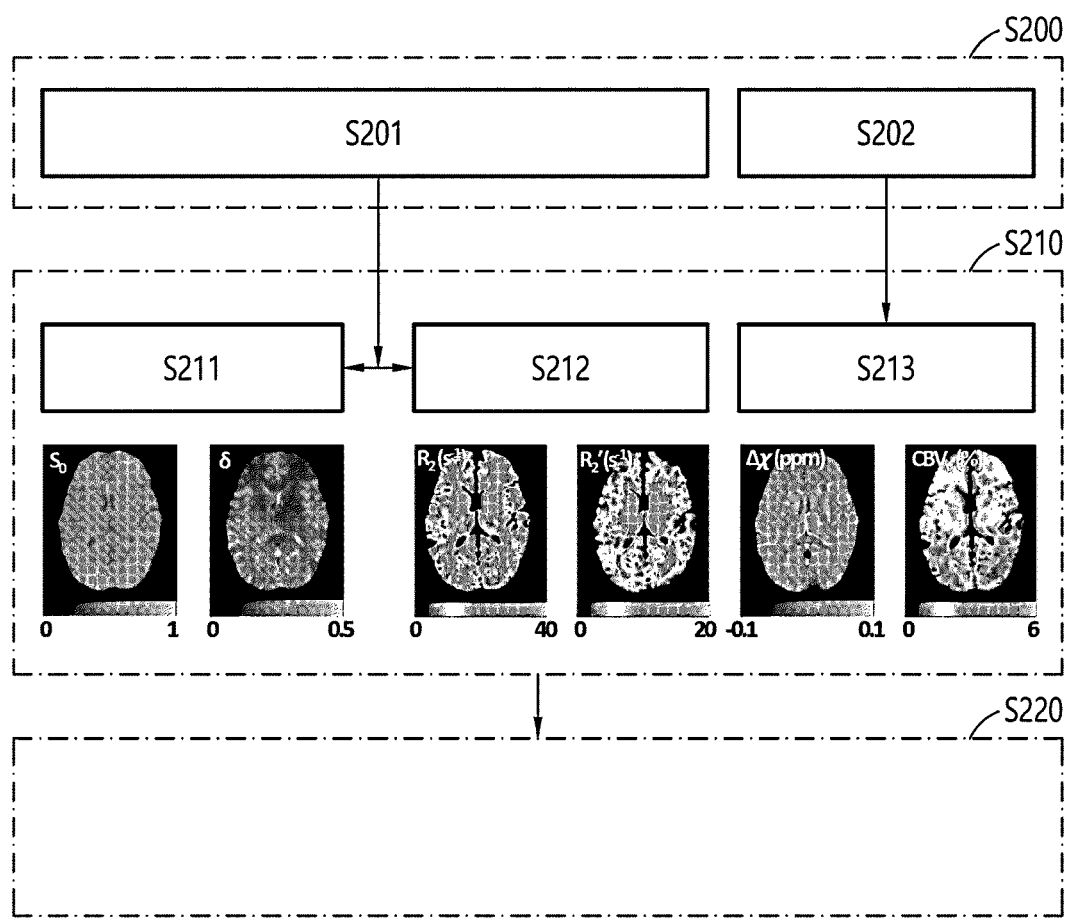
FIG. 2 and FIG. 3 illustrate a magnetic resonance imaging method for precisely measuring cerebral oxygen metabolism according to an embodiment of the present disclosure.

FIG. 2 illustrates a magnetic resonance imaging method for precisely measuring cerebral oxygen metabolism according to an embodiment of the present disclosure.

FIG. 2 illustrates a procedure in which the magnetic resonance imaging method for precisely measuring cerebral oxygen metabolism according to an embodiment of the present disclosure maps a quantitative model parameter based on pre-processed data.

Referring to FIG. 2, the magnetic resonance imaging method for precisely measuring cerebral oxygen metabolism according to an embodiment of the present disclosure includes a data acquiring step S200, a data pre-processing step S210, and a quantitative model processing step S220.

According to one embodiment of the present disclosure, the data acquiring step S200 acquires a steady-state free precession-based image data capable of simultaneously mapping R2, R2', and the susceptibility (χ) over the entire brain in a 3 dimensional manner in a step S201.

In this regard, the steady-state free precession-based image data refers to AUSFIDE image data. AUSFIDE (alternating unbalanced SSFP-FID & SSFP-ECHO) is based on an unbalanced SSFP class pulse train while integrating z-shimming into multi-echo sampling.

AUSFIDE (alternating unbalanced SSFP-FID & SSFP-ECHO) represents two unbalanced SSFP configurations including SSFP-FID and SSFP-ECHO in an alternating manner in successive TR periods.

A plurality of gradient recalled signals may be sampled in each mode of SSFP to capture temporal signal decay as expressed by a velocity constant R2+R2' and R2−R2' for SSFP-FID and SSFP ECHO.

Steady-state free precession (SSFP)-based image data is capable of acquiring 3-dimensional image data at a faster speed than an existing R2 and R2' measurement method, and may provide additional quantitative susceptibility information therefrom.

Furthermore, z-shimming inserted echo sequence and a model-based signal correction method may be combined with each other to allow parameter measurement to be adjusted to be less sensitive to magnetic field imperfection.

The steady-state-free-precession (SSFP)-based image data may be referred to as the alternating unbalanced SSFP-FID & SSFP-ECHO (AUSFIDE) image data.

In one example, the alternating unbalanced SSFP-FID & SSFP-ECHO (AUSFIDE) image data may be obtained by collecting SSFP-FID and SSFP-ECHO signals alternately and may allow rapid 3D encoding of both R2 and R2'.

Furthermore, inherent sensitivity of a scheme based on a large induced magnetic field offset ($\Delta B_0$) may be addressed via 3D z-shimming and voxel-spread-function (VSF)-based correction.

According to one embodiment of the present disclosure, the data acquiring step S200 acquires the VS-VSL (velocity-selective venous spin labeling) image data in the step S202.

The VS-VSL image data may be related to imaging technology that may measure the cerebral blood volume throughout the brain in the three dimensional manner.

The VS-VSL image data exhibit very robust properties to the non-uniformity of the main magnetic field when compared to the conventional gas calibration-based scheme.

In particular, the VS-VSL image data may directly measure the cerebral blood volume based on an endogenous signal source, and thus eliminate the need for additional equipment such as a gas delivery system, and the imaging target may be comfortable for experimentation.

In other words, the magnetic resonance imaging method for precisely measuring cerebral oxygen metabolism according to an embodiment of the present disclosure acquires the AUSFIDE (alternating unbalanced SSFP-FID & SSFP-ECHO) image data and the VS-VSL image data in the data acquiring step S200.

In the data pre-processing step S210, the magnetic resonance imaging method for precisely measuring cerebral oxygen metabolism according to an embodiment of the present disclosure may pre-process a size and a phase of the AUSFIDE (alternating unbalanced SSFP-FID & SSFP-ECHO) image data and then may process size-related preliminary information data and phase-related preliminary information data, and may process the CBVv information data based on the VS-VSL image data.

Specifically, the data pre-processing step S210 pre-processes a size of the AUSFIDE (alternating unbalanced SSFP-FID & SSFP-ECHO) image data in a step S211.

The step S211 alternately collects SSFP-FID and SSFP-ECHO signals from the AUSFIDE (alternating unbalanced SSFP-FID & SSFP-ECHO) image data and processes R2 and R2' as size-related preliminary information data based on the alternately collected SSFP-FID and SSFP-ECHO signals.

In other words, the step S211 may alternately collect the SSFP-FID and SSFP-ECHO signals using $S_0$ and $\delta$ based on the AUSFIDE (alternating unbalanced SSFP-FID & SSFP-ECHO) image data and may process R2 and R2' as size-related preliminary information based on the alternately collected SSFP-FID and SSFP-ECHO signals.

For example, the SSFP-FID signal may be the sum of R2 and R2', and the SSFP-ECHO signal may be a value obtained by subtracting R2' from R2.

The step S211 determines preliminary information data corresponding to a voxel susceptibility as $\Delta\chi$, based on a large induced magnetic field offset ($\Delta B_0$) via 3D z-shimming and the voxel spread function (VSF)-based correction in the AUSFIDE (alternating unbalanced SSFP-FID & SSFP-ECHO) image data.

In other words, the magnetic resonance imaging method for precisely measuring cerebral oxygen metabolism according to an embodiment of the present disclosure may determine R2 and R2', and $\Delta\chi$ as parameters to be pre-processed, based on the AUSFIDE (alternating unbalanced SSFP-FID & SSFP-ECHO) image data.

Further, a step S213 may process the CBVv information data based on the VS-VSL image data.

That is, the data pre-processing step S210 may pre-process R2, R2', $\Delta\chi$, and CBVv as the preliminary information data.

The data pre-processing step S210 may acquire image data by pre-processing the RF-irreversible transverse relaxation rate constant R2, the RF-reversible transverse relaxation rate constant R2', and $\Delta\chi$ and CBVv as the preliminary information data.

According to one embodiment of the present disclosure, the quantitative model processing step S220 may derive the venous blood oxygen saturation level and the deoxygenated blood volume (DBV), based on the preliminary information data acquired via the pre-processing in the data pre-processing step S210.

More specifically, the quantitative model processing step S220 may derive the venous blood oxygen saturation level and the deoxygenated blood volume (DBV) based on the Mathematical Relationship 3.

Figure 3:
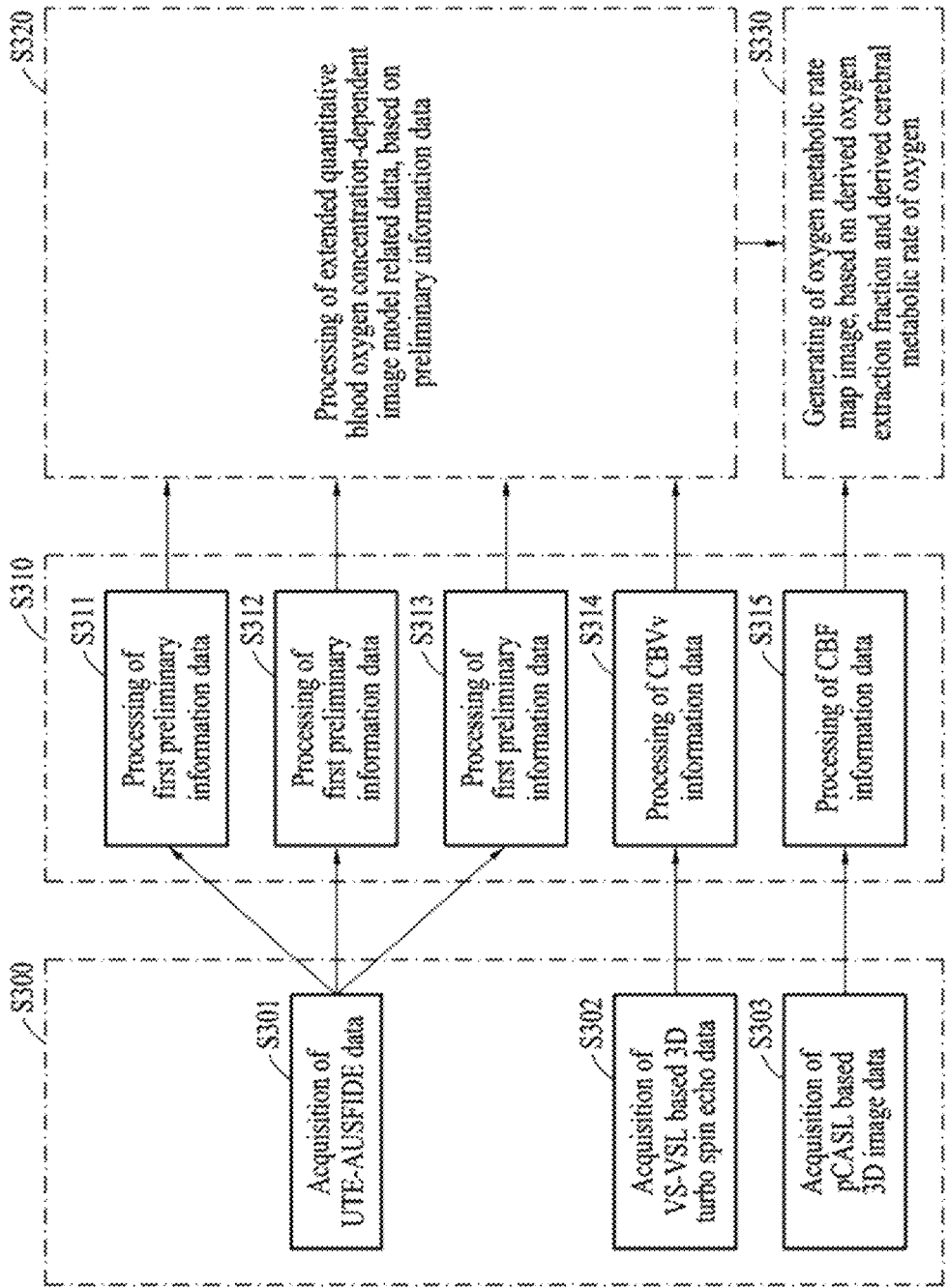

FIG. 3 illustrates a magnetic resonance imaging method for precisely measuring cerebral oxygen metabolism according to an embodiment of the present disclosure.

FIG. 3 illustrates a magnetic resonance imaging method for precisely measuring cerebral oxygen metabolism which additionally acquires the image data in ultrashort echo-time (UTE) and acquires the UTE-AUSFIDE data based on a UTE-AUSFIDE pulse train design in which the image data may be mapped to a spherical k-space along a 3D full radial trajectory.

Referring to FIG. 3, the magnetic resonance imaging method for precisely measuring cerebral oxygen metabolism according to an embodiment of the present disclosure includes a data acquiring step S300, a data pre-processing step S310, a quantitative model processing step S320, and a magnetic resonance image generation step S330.

According to one embodiment of the present disclosure, the data acquiring step S300 may acquire the UTE-AUSFIDE data in a step S301, and may acquire the VS-VSL-based 3-dimensional turbo spin echo data at a step S302, and may acquire pCASL (3D pseudo-continuous arterial spin labeling)-based 3-dimensional image data in a step S303.

Specifically, the data acquiring step S300 additionally acquires the image data from the AUSFIDE pulse train in the ultrashort echo-time (UTE) in the step S301, and acquires the UTE-AUSFIDE data based on the design of the UTE-AUSFIDE pulse train in which the image data may be mapped to the spherical k-space along a 3D full radial trajectory.

In this regard, the AUSFIDE pulse train may be used to acquire steady-state free precession-based image data capable of simultaneous mapping of R2, R2', and susceptibility over the entire brain in the 3 dimensional manner. The steady-state-free-precession (SSFP)-based image data is capable of acquiring 3-dimensional image data at a higher speed compared to the existing R2 and R2' measurement scheme, and thus may provide additional quantitative susceptibility information therefrom.

For example, the UTE-AUSFIDE data may be used to process the first to third preliminary information data.

Furthermore, the UTE-AUSFIDE data may improve the image resolution in the longitudinal direction via the 3D full radial k-space mapping, thereby deriving an isotropic high-resolution parameter map, and may have a reduced level of signal distortion due to non-spontaneous movement in the imaging target such as blood flow or cerebrospinal fluid flow, and may use the ultrashort echo-time signal instead of spin echo information in the qBOLD model as a quantitative model, thereby improving quantitative model signal analysis performance without increasing a total imaging time.

For example, in the UTE-AUSFIDE data, a TX/RX switching time as a variable directly related to the stability of the UTE signal varies depending on the characteristics of the scanner. Thus, the image data may be acquired while changing a UTE signal acquisition start time from 20 us to 100 us at 10 us intervals.

It is desirable to select a value that produces results with the highest signal-to-noise ratio and image quality via image reconstruction of each image data. Using the selected parameter, additional image data about a non-uniform aqueous solution phantom containing a magnetic material may be acquired.

The data acquiring step S300 acquires VS-VSL-based 3-dimensional turbo spin echo data at a step S302. In this regard, the VS-VSL image data may be related to an imaging scheme that may measure the cerebral blood volume across the entire brain in a 3D manner.

The VS-VSL image data may directly measure the cerebral blood volume based on an endogenous signal source, and thus eliminate the need for additional equipment such as a gas delivery system, and the imaging target may be comfortable for experimentation.

The data acquiring step S300 acquires the pCASL image data to estimate the CBF (cerebral blood flow) in a step S303.

For example, the pCASL image data may be used to acquire a 3-dimensional high-resolution oxygen metabolic rate map across the entire brain at an isotropic voxel size of 1.5 mm.

The data pre-processing step S310 according to an embodiment of the present disclosure may process the first to third preliminary information data based on the UTE-AUSFIDE data in the steps S311 to S313 to estimate the preliminary information data for the quantitative model processing.

Furthermore, the data pre-processing step S310 may estimate the CBVv information data based on the VS-VSL image data in a step S314.

Furthermore, the data pre-processing step S310 may estimate the CBF information data based on the pCASL image data in a step S315.

The 3-dimensional quantitative map of the $CMRO_2$ may be acquired using the CBF information data, the arterial blood oxygen saturation level (Ya) based on pulse oximetry, and Yv based on the Mathematical Relationship 3 according to the Fick's principle of the Mathematical Relationship 1.

The quantitative model processing step S320 according to an embodiment of the present disclosure processes extended quantitative blood oxygen concentration-dependent image model related data, based on the preliminary information data.

Specifically, the quantitative model processing step S320 may process the quantitative model to map the qBOLD parameter by obtaining the solution to the constrained nonlinear inverse calculation problem on a voxel basis, based on the multi-echo UTE-AUSFIDE image data, the preliminary information data as the three types of measurement parameters ABO, R2, R2', and X based on the UTE-AUSFIDE image data, and the separately acquired VS-VSL-based cerebral blood volume (CBVv) information data, according to the Mathematical Relationship 3.

According to one embodiment of the present disclosure, the magnetic resonance image generation step S330 may generate the oxygen metabolic rate map image as a magnetic resonance image based on the derived oxygen extraction fraction and the derived cerebral metabolic rate of oxygen ($CMRO_2$).

In one example, the magnetic resonance image generation step S330 derives the oxygen extraction fraction based on a following Mathematical Relationship 9 and derives the cerebral metabolic rate of oxygen ($CMRO_2$) based on a following Mathematical Relationship 10:

$$OEF = (Y_a - Y_v)/Y_a \quad \text{[Mathematical Relationship 9]}$$

In the Mathematical Relationship 9, OEF may represent the oxygen extraction fraction, Ya may represent the arterial blood oxygen saturation level based on pulse oximetry, and Yv may represent a parameter derived based on the Mathematical Relationship 3 in the quantitative model processing step S320.

For example, Ya/Yv (unit: percent) may represent the arterial blood hemoglobin oxygen saturation level/the venous blood hemoglobin oxygen saturation level.

$$CMRO_2 = C_a \cdot CBF \cdot OEF \cdot Y_a \quad \text{[Mathematical Relationship 10]}$$

In the Mathematical Relationship 10, $CMRO_2$ may represent the cerebral metabolic rate of oxygen, Ca may represent the oxygen capacity of the arterial blood, Ya may represent the arterial blood oxygen saturation level based on pulse oximetry, and OEF may represent the oxygen extraction fraction.

According to one embodiment of the present disclosure, the magnetic resonance image generation step S330 may generate the magnetic resonance image corresponding to the 3-dimensional high-resolution oxygen metabolic rate maps across the entire brain, based on the first preliminary information data to third preliminary information data, the CBVv information data, and the CBF information data estimated based on the UTE-AUSFIDE data, the VS-VSL image data, and the 3D pCASL image data at an isotropic 1.5 mm voxel size of each of the UTE-AUSFIDE data and the 3D pCASL image data.

Further, the process of estimating the CBVv from the VS-VSL image data is repeatedly updated in the process of solving the qBOLD problem.

The calculated CBVv image data may be re-sectioned to have a target voxel size of 1.5 mm via a registration process. When the CBF information data has been obtained from the pCASL image data, the magnetic resonance image as a 3-dimensional quantitative map of the $CMRO_2$ may be generated based on the CBF information data, the arterial blood oxygen saturation level (Ya) based on the pulse oximetry and Yv based on the Mathematical Relationship 3 according to the Fick's principle of Mathematical Relationship 1.

Therefore, the method and the device of the present disclosure may generate the magnetic resonance image based on a high-speed 3-dimensional magnetic resonance pulse train that may simultaneously measure the RF (resonance frequency) inversible or RF-irreversible transverse relaxation rate constant and the susceptibility.

The method and the device of the present disclosure may generate the magnetic resonance image capable of distinguishing the contribution of the RF-reversible transverse relaxation rate constant of the non-heme iron and the contribution of the RF-reversible transverse relaxation rate constant of the heme iron from each other, and accurately distinguishing the cerebral blood volume and the venous blood oxygen saturation level from each other.

Figure 4:
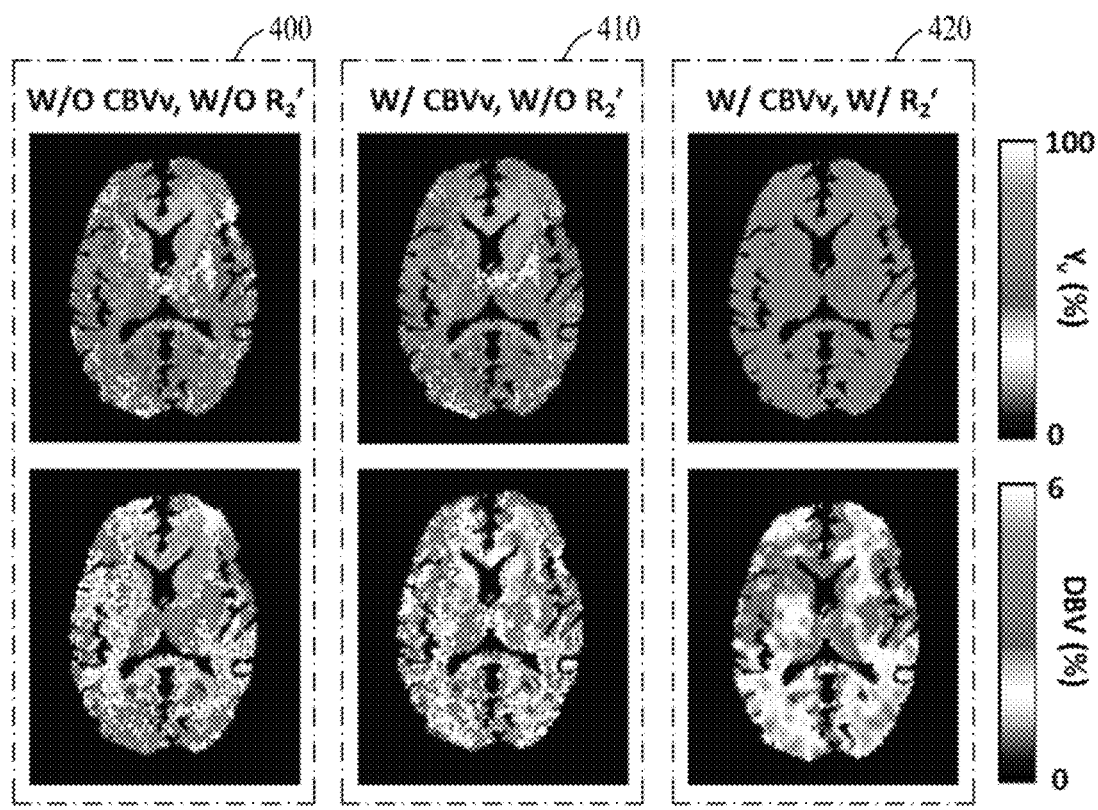
FIG. 4 and FIG. 5 illustrate a 3-dimensional brain map for precisely measuring cerebral oxygen metabolism according to an embodiment of the present disclosure.
Figure 5:
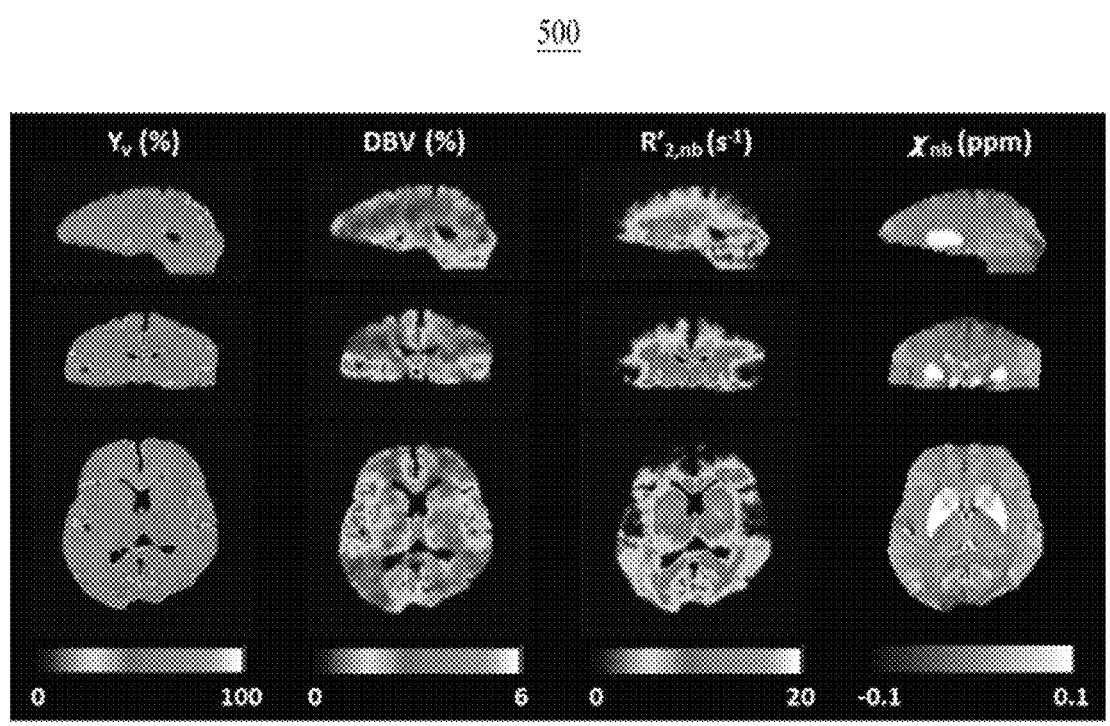

FIG. 4 and FIG. 5 illustrate a 3-dimensional brain map for precisely measuring cerebral oxygen metabolism according to an embodiment of the present disclosure.

FIG. 4 illustrates a pair Yv and DBV maps of an axial plane as derived via three different schemes using pre-estimation of R2' and CBVv from the magnetic resonance image corresponding to a 3-dimensional brain map for precisely measuring cerebral oxygen metabolism according to an embodiment of the present disclosure.

An image 400 is directed to a case in which both R2' and CBVv are not used, an image 410 is directed to a case in which R2' is used and CBVv is not used, and an image 420 is directed to a case in which both R2' and CBVv are used.

In the images 400 and 410, when there is no CBVv or R2' preliminary information data, both DBV and Yv maps have artificial values in many voxels.

On the contrary, in the image 420, when both CBVv and R2' preliminary information data are present, the qBOLD problem is greatly stabilized, such that a magnetic resonance image map in which the estimated Yv and DBV are within a physiologically possible range is generated.

FIG. 5 illustrates, as a magnetic resonance image, an entire 3-dimensional map of Yv, DBV, $R'2_{nb}$ and $\chi_{nb}$ in three orthogonal planes as a 3-dimensional brain map for precisely measuring cerebral oxygen metabolism according to an embodiment of the present disclosure.

Referring to an image 500, the group averages of Yv and DBV in gray and white areas may be as follows: Yv=64.1±1.7% and 63.7±1.7% in the gray and white areas, respectively, and DBV=2.6±0.6% and 1.7±0.5% in the gray and white areas, respectively.

Therefore, the method and the device of present disclosure may improve an image resolution in a longitudinal direction to derive an isotropic high-resolution parameter map, and generate an image with a reduced level of signal distortion due to non-spontaneous movement in the imaging target such as blood flow or cerebrospinal fluid flow, and acquire the UTE (ultrashort echo-time) signal, and thus improve the qBOLD (quantitative blood oxygen level dependent) model signal analysis performance without increasing a total imaging time using the acquired UTE signal instead of the spin echo information required in the process of processing the qBOLD (quantitative blood oxygen level dependent) model as the quantitative model.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions.

The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

Although the present invention has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

The invention claimed is:

1. A magnetic resonance imaging device for precisely measuring cerebral oxygen metabolism, the device comprising a memory configured to store computer-readable instructions and one or more processors configured to execute the computer-readable instructions such that the one or more processors are configured to:
   acquire UTE (ultrashort echo-time)-AUSFIDE (alternating unbalanced SSFP-FID & SSFP-ECHO) image data, VS-VSL (velocity-selective venous spin labeling) image data, and pCASL (pseudo-continuous arterial spin labeling) image data;
   process a plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data, and to process CBF (cerebral blood flow) information data based on the acquired pCASL (pseudo-continuous arterial spin labeling) image data;
   acquire variable information (Yv) to derive an oxygen extraction fraction (OEF) and a cerebral metabolic rate of oxygen ($CMRO_2$) in order to acquire a 3-dimensional oxygen metabolic rate map of an entire brain using the processed plurality of preliminary information data; and
   derive the oxygen extraction fraction (OEF) and the cerebral metabolic rate of oxygen ($CMRO_2$) using the acquired variable information and to generate an oxygen metabolic rate map image as a magnetic resonance image, based on the derived oxygen extraction fraction (OEF) and the derived cerebral metabolic rate of oxygen ($CMRO_2$),
   wherein the one or more processors are configured to process cerebral blood volume (CBVv) information data among the plurality of preliminary information data, based on the VS-VSL (velocity-selective venous spin labeling) image data.

2. The magnetic resonance imaging device of claim 1, wherein the one or more processors are configured to acquire the UTE (ultrashort echo-time)-AUSFIDE (alternating unbalanced SSFP-FID & SSFP-ECHO) image data to estimate at least one of an RF-reversible transverse relaxation rate constant, an RF-irreversible transverse relaxation rate constant, a susceptibility, and an induced magnetic field offset.

3. The magnetic resonance imaging device of claim 2, wherein the one or more processors are configured to:
   process the induced magnetic field offset based on a voxel spread function (VSF) as first preliminary information data among the plurality of preliminary information data, using the acquired UTE (ultrashort echo-time)-AUSFIDE (alternating unbalanced SSFP-FID & SSFP-ECHO) image data;
   alternately collect a SSFP-FID signal and a SSFP-ECHO signal and process the RF-reversible transverse relaxation rate constant and the RF-irreversible transverse relaxation rate constant as second preliminary information data thereof, using the alternately collected SSFP-FID signal and a SSFP-ECHO signal; and process the susceptibility as third preliminary information data thereof, based on quantitative susceptibility mapping (QSM).

4. The magnetic resonance imaging device of claim 1, wherein the one or more processors are configured to apply the plurality of preliminary information data to a following Mathematical Relationship 3 to acquire the variable information (Yv) so as to include a contribution distinguishing term distinguishing a contribution of an RF-reversible transverse relaxation rate constant of a non-heme iron and a contribution of the RF-reversible transverse relaxation rate constant of a heme iron from each other:

$$\mathrm{argmin} \sum_t \|y(t) - \Xi(\Theta, t)\|_2^2 + w\|\chi - \Psi(\Theta)\|_2^2 + p\|R_2' - \Upsilon(\Theta)\|_2^2.$$ [Mathematical Relationship 3]

wherein in the Mathematical Relationship 3, y(t) represents the sampling time of the AUSFIDE (alternating unbalanced SSFP-FID & SSFP-ECHO) image data signal, $\Theta = \{S_{FID}, S_{ECHO}\}$ represents a description of R2 and R2', $\Psi$ represents a four pool decomposition model for Y that distinguishes the contribution of the R2' of non-blood ($R'_{2,nb}$) and the contribution of the R2' of deoxygenated blood (DBV) from each other, w and p represent normalization parameters that apply preliminary knowledge in qBOLD parameter estimation, $\theta = \{Yv, CBVv, R2, nh, xnb\}$ represents a set of unknowns, and $\gamma$ represents the term for distinguishing the contribution of the RF-reversible transverse relaxation rate constant R2' of the non-heme iron (nh) and the contribution of the RF-reversible transverse relaxation rate constant R2' of the heme iron (h) from each other.

5. The magnetic resonance imaging device of claim 4, wherein the one or more processors are configured to acquire the contribution distinguishing term using a following Mathematical Relationship 5 in acquiring the variable information (Yv) based on the Mathematical Relationship 3:

$$Y = R'_{2,nh} + R'_{2,h}; R'_{2,h} \propto CBV_v \cdot (1 - Y_v).$$ [Mathematical Relationship 5]

wherein in the Mathematical Relationship 5, $\gamma$ distinguishes the contribution of R2' of non-blood and the contribution of R2' of deoxygenated blood from each other, and R2'(R'2,h) of the deoxygenated blood is correlated with CBVv and Yv.

6. The magnetic resonance imaging device of claim 5, wherein the one or more processors are configured to derive the oxygen extraction fraction (OEF) using an arterial blood oxygen saturation level (Ya) based on pulse oximetry, and the variable information (Yv).

7. The magnetic resonance imaging device of claim 6, wherein the one or more processors are configured to derive the cerebral metabolic rate of oxygen ($CMRO_2$) using the processed CBF (cerebral blood flow) information data, the derived oxygen extraction fraction (OEF), an oxygen capacity (Ca) of arterial blood, and the variable information (Yv).

8. A magnetic resonance imaging method for precisely measuring cerebral oxygen metabolism, the method comprising:

acquiring, by one or more processors, UTE (ultrashort echo-time)-AUSFIDE (alternating unbalanced SSFP-FID & SSFP-ECHO) image data, VS-VSL (velocity-selective venous spin labeling) image data, and pCASL (pseudo-continuous arterial spin labeling) image data;

processing, by the one or more processors, a plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data, and processing, by the one or more processors, CBF (cerebral blood flow) information data based on the acquired pCASL (pseudo-continuous arterial spin labeling) image data;

acquiring, by the one or more processors, variable information (Yv) to derive an oxygen extraction fraction (OEF) and a cerebral metabolic rate of oxygen ($CMRO_2$) in order to acquire a 3-dimensional oxygen metabolic rate map of an entire brain using the processed plurality of preliminary information data; and deriving, by the one or more processors, the oxygen extraction fraction (OEF) and the cerebral metabolic rate of oxygen ($CMRO_2$) using the acquired variable information and generating, by the one or more processors, an oxygen metabolic rate map image as a magnetic resonance image, based on the derived oxygen extraction fraction (OEF) and the derived cerebral metabolic rate of oxygen ($CMRO_2$), wherein processing, by the one or more processors, the plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data includes:

processing, by the one or more processors, cerebral blood volume (CBVv) information data among the plurality of preliminary information data, based on the VS-VSL (velocity-selective venous spin labeling) image data.

9. The magnetic resonance imaging method of claim 8, wherein acquiring, by the one or more processors, the UTE (ultrashort echo-time)-AUSFIDE (alternating unbalanced SSFP-FID & SSFP-ECHO) image data, the VS-VSL (velocity-selective venous spin labeling) image data, and the pCASL (pseudo-continuous arterial spin labeling) image data includes:

acquiring, by the one or more processors, the UTE (ultrashort echo-time)-AUSFIDE (alternating unbalanced SSFP-FID & SSFP-ECHO) image data to estimate at least one of an RF-reversible transverse relaxation rate constant, an RF-irreversible transverse relaxation rate constant, a susceptibility, and an induced magnetic field offset.

10. The magnetic resonance imaging method of claim 9, wherein processing, by the one or more processors, the plurality of preliminary information data for quantitative model processing, based on the acquired UTE (ultrashort echo-time)-AUSFIDE (alternating unbalanced SSFP-FID & SSFP-ECHO) image data and the acquired VS-VSL (velocity-selective venous spin labeling) image data includes:

processing, by the one or more processors, the induced magnetic field offset based on a voxel spread function (VSF) as first preliminary information data among the plurality of preliminary information data, using the acquired UTE (ultrashort echo-time)-AUSFIDE (alternating unbalanced SSFP-FID & SSFP-ECHO) image data;

alternately collecting, by the one or more processors, a SSFP-FID signal and a SSFP-ECHO signal and processing, by the data pre-processing unit, the RF-reversible transverse relaxation rate constant and the RF-irreversible transverse relaxation rate constant as second preliminary information data thereof, using the alternately collected SSFP-FID signal and a SSFP-ECHO signal; and processing, by the one or more processors, the susceptibility as third preliminary information data thereof, based on quantitative susceptibility mapping (QSM).

11. The magnetic resonance imaging method of claim 8, wherein acquiring, by the one or more processors, the variable information (Yv) to derive the oxygen extraction fraction (OEF) and the cerebral metabolic rate of oxygen (CMRO$_2$) in order to acquire the 3-dimensional oxygen metabolic rate map of an entire brain using the processed plurality of preliminary information data includes:

applying, by the one or more processors, the plurality of preliminary information data to a following Mathematical Relationship 3 to acquire the variable information (Yv) so as to include a contribution distinguishing term distinguishing a contribution of an RF-reversible transverse relaxation rate constant of a non-heme iron and a contribution of the RF-reversible transverse relaxation rate constant of a heme iron from each other:

$$\mathrm{argmin} \sum_t \|y(t) - \Xi(\Theta, t)\|_2^2 + w\|\chi - \Psi(\Theta)\|_2^2 + p\|R_2' - \Upsilon(\Theta)\|_2^2.$$ [Mathematical Relationship 3]

wherein in the Mathematical Relationship 3, y(t) represents the sampling time of the AUSFIDE (alternating unbalanced SSFP-FID & SSFP-ECHO) image data signal, $\Theta=\{S_{FID}, S_{ECHO}\}$ represents a description of R2 and R2', $\Psi$ represents a four pool decomposition model for Y that distinguishes the contribution of the R2' of non-blood (R'2,nb) and the contribution of the R2' of deoxygenated blood (DBV) from each other, w and p represent normalization parameters that apply preliminary knowledge in qBOLD parameter estimation, θ={Yv,CBVv,R2,nh,xnb} represents a set of unknowns, and γ represents the term for distinguishing the contribution of the RF-reversible transverse relaxation rate constant R2' of the non-heme iron (nh) and the contribution of the RF-reversible transverse relaxation rate constant R2' of the heme iron (h) from each other.

12. The magnetic resonance imaging device of claim 11, wherein acquiring, by the one or more processors, the variable information (Yv) to derive the oxygen extraction fraction (OEF) and the cerebral metabolic rate of oxygen (CMRO$_2$) in order to acquire the 3-dimensional oxygen metabolic rate map of an entire brain using the processed plurality of preliminary information data includes:

acquiring, by the one or more processors, the contribution distinguishing term using a following Mathematical Relationship 5 in acquiring the variable information (Yv) based on the Mathematical Relationship 3:

$$\Upsilon = R'_{2,nh} + R'_{2,h}; R'_{2,h} \propto CBV_v \cdot (1 - Y_v).$$ [Mathematical Relationship 5]

wherein in the mathematical Relationship 5, γ distinguishes the contribution of R2' of non-blood and the contribution of R2' of deoxygenated blood from each other, and R2'(R'2,h) of the deoxygenated blood is correlated with CBVv and Yv.

13. The magnetic resonance imaging device of claim 12, wherein deriving, by the one or more processors, the oxygen extraction fraction (OEF) and the cerebral metabolic rate of oxygen (CMRO$_2$) using the acquired variable information and generating, by the one or more processors, the oxygen metabolic rate map image as the magnetic resonance image, based on the derived oxygen extraction fraction (OEF) and the derived cerebral metabolic rate of oxygen (CMRO$_2$) include:

deriving, by the one or more processors, the oxygen extraction fraction (OEF) using an arterial blood oxygen saturation level (Ya) based on pulse oximetry, and the variable information (Yv); and deriving, by the one or more processors, the cerebral metabolic rate of oxygen (CMRO$_2$) using the processed CBF (cerebral blood flow) information data, the derived oxygen extraction fraction (OEF), an oxygen capacity (Ca) of arterial blood, and the variable information (Yv).

* * * * *